US005254108A

United States Patent [19]

Burrell et al.

[11] Patent Number: 5,254,108

[45] Date of Patent: Oct. 19, 1993

[54] ROLLER APPLICATOR

[75] Inventors: Anthony I. Burrell, Avoca Beach; Glen W. Bunyan, Kanwal; Ian R. Phillips, Killara, all of Australia

[73] Assignee: N. J. Phillips Pty. Limited, Somersby, Australia

[21] Appl. No.: 821,702

[22] Filed: Jan. 16, 1992

[51] Int. Cl.[5] ..................... A61M 35/00

[52] U.S. Cl. ..................... 604/289; 222/249; 239/447; 401/147; 401/220

[58] Field of Search ..................... 604/289, 310, 311; 222/249, 376; 239/62, 93, 99, 100, 436, 447; 401/147, 197, 219, 220

[56] References Cited

U.S. PATENT DOCUMENTS

| | | | |
|---|---|---|---|
| 2,757,044 | 7/1956 | Gerbracht | 239/62 |
| 3,620,633 | 11/1971 | Charvoz | 401/147 |
| 4,732,503 | 3/1988 | Bader et al. | 401/197 |
| 4,943,176 | 7/1990 | Baker | 401/197 |
| 5,060,824 | 10/1991 | Credle, Jr. | 222/249 X |

FOREIGN PATENT DOCUMENTS

| | | | |
|---|---|---|---|
| 615935 | 10/1991 | Australia . | |
| 0601859 | 5/1948 | United Kingdom . | |
| 2088487 | 6/1982 | United Kingdom . | |
| 2160105 | 12/1985 | United Kingdom | 604/289 |

*Primary Examiner*—Randall L. Green
*Assistant Examiner*—Mary Beth O. Jones
*Attorney, Agent, or Firm*—Ladas & Parry

[57] ABSTRACT

An applicator to apply a medication in liquid form to the skin or fleece of an animal. The applicator his a handle to be gripped by a user to move the applicator over the skin or fleece. Rotatably supported by the handle is a roller which is equipped with a cam track. Received within the cam track is a cam follower which causes reciprocation of a piston within a cylinder. The cylinder and piston co-operate to pump the liquid to a nozzle so that application of the liquid is metered in accordance with rotation of the roller.

25 Claims, 7 Drawing Sheets

ROLLER APPLICATOR

TECHNICAL FIELD

The present invention relates to liquid applicators employing a roller, and more particularly but not exclusively to an applicator to apply a medication to animals.

BACKGROUND OF THE INVENTION

Some medications, are easily and most efficiently delivered to an animal by applying the medication to the skin or fleece of the animal. In the past, the medication has usually been sprayed onto the animal or in some instances has been applied by a brush.

The above discussed methods have the disadvantage that the amount of material is not metered ana accordingly it is easy for the animal to receive insufficient medication, or more often, an overdose of the medication.

OBJECT OF THE INVENTION

It is the object of the present invention to overcome or substantially ameliorate the above disadvantages.

SUMMARY OF THE INVENTION

There Is disclosed herein an applicator comprising:

a body to be passed over a surface to which a fluid is to be applied by the applicator;

relative movement responsive means actuated upon relative movement between said body and surface;

delivery means directed in use to deliver said fluid to said surface; and pump means communicating with said delivery weans to deliver the fluid under pressure thereto, said pump means being operatively associated with said movement, responsive means so as to deliver fluid to said delivery means, actuation of said movement responsive means upon actuation of said movement responsive means.

BRIEF DESCRIPTION OF THE DRAWINGS

A preferred form of the present invention will now be described by way of example with reference to the accompanying drawings wherein.

DESCRIPTION OF THE PREFERRED EMBODIMENTS

Figure 1:
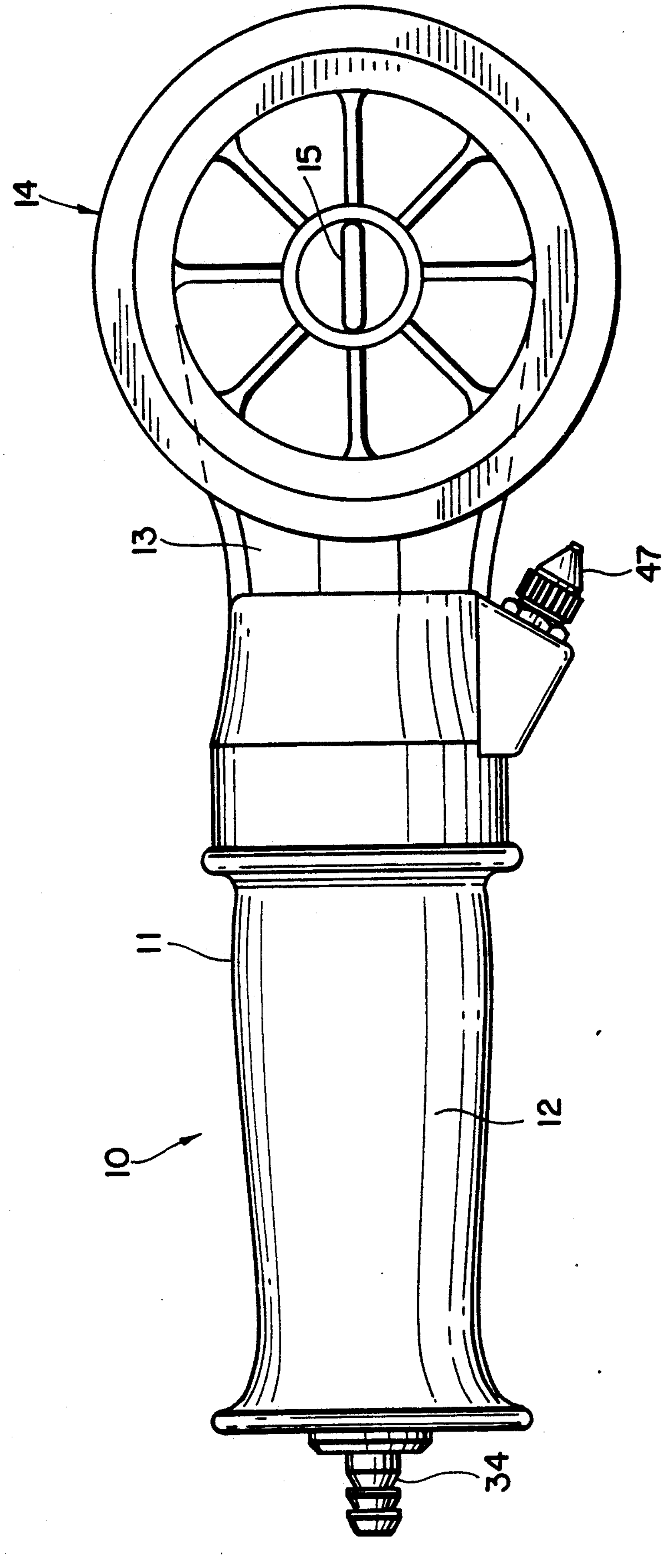
FIG. 1 is a schematic side elevation of an applicator to deliver medication to an animal.
Figure 2:
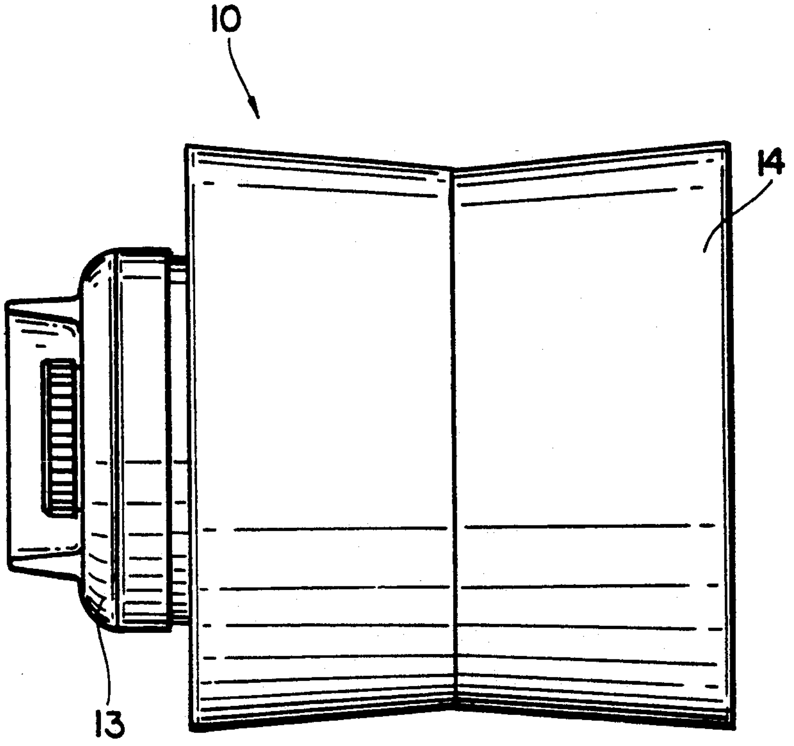
FIG. 2 is a schematic end elevation of the applicator of FIG. 1.
Figure 5:
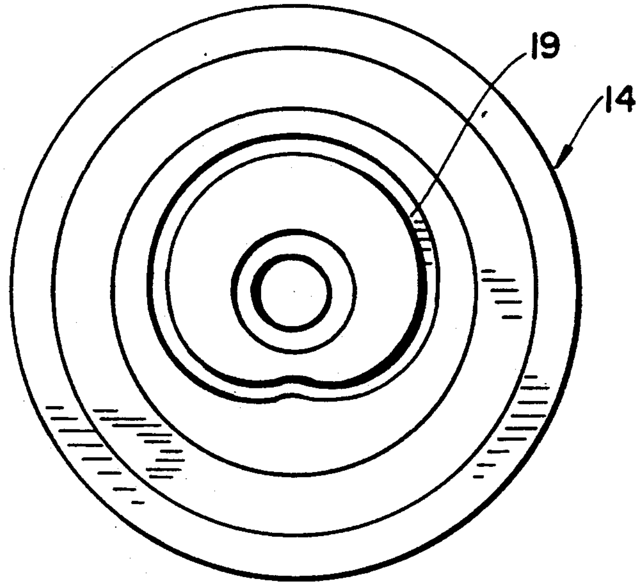
FIG. 5 is a schematic end elevation of a portion of the roller employed in the applicator of FIG. 1.
Figure 3:
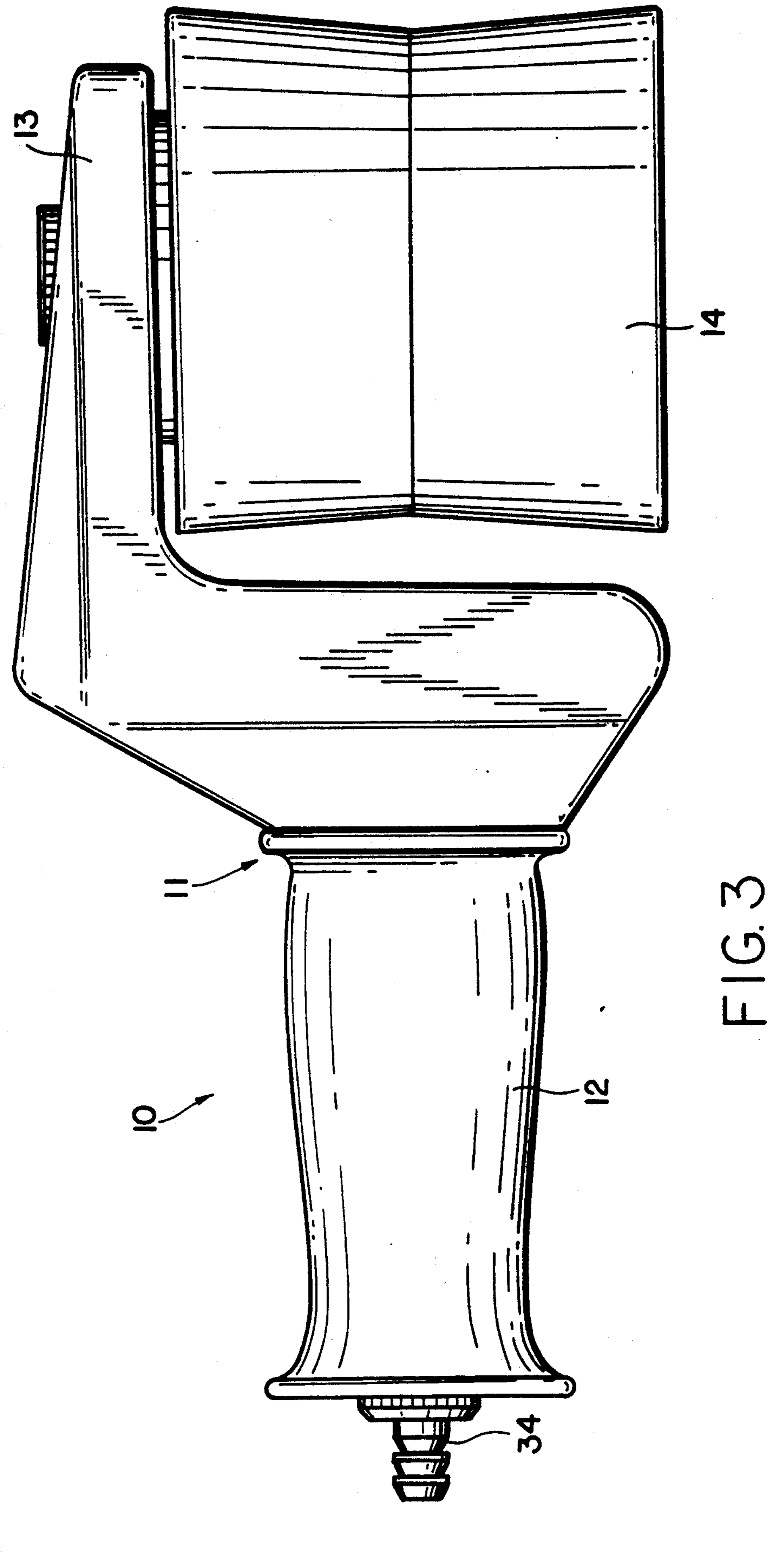
FIG. 3 is a schematic top plan view of the applicator of FIG. 1.
Figure 4:
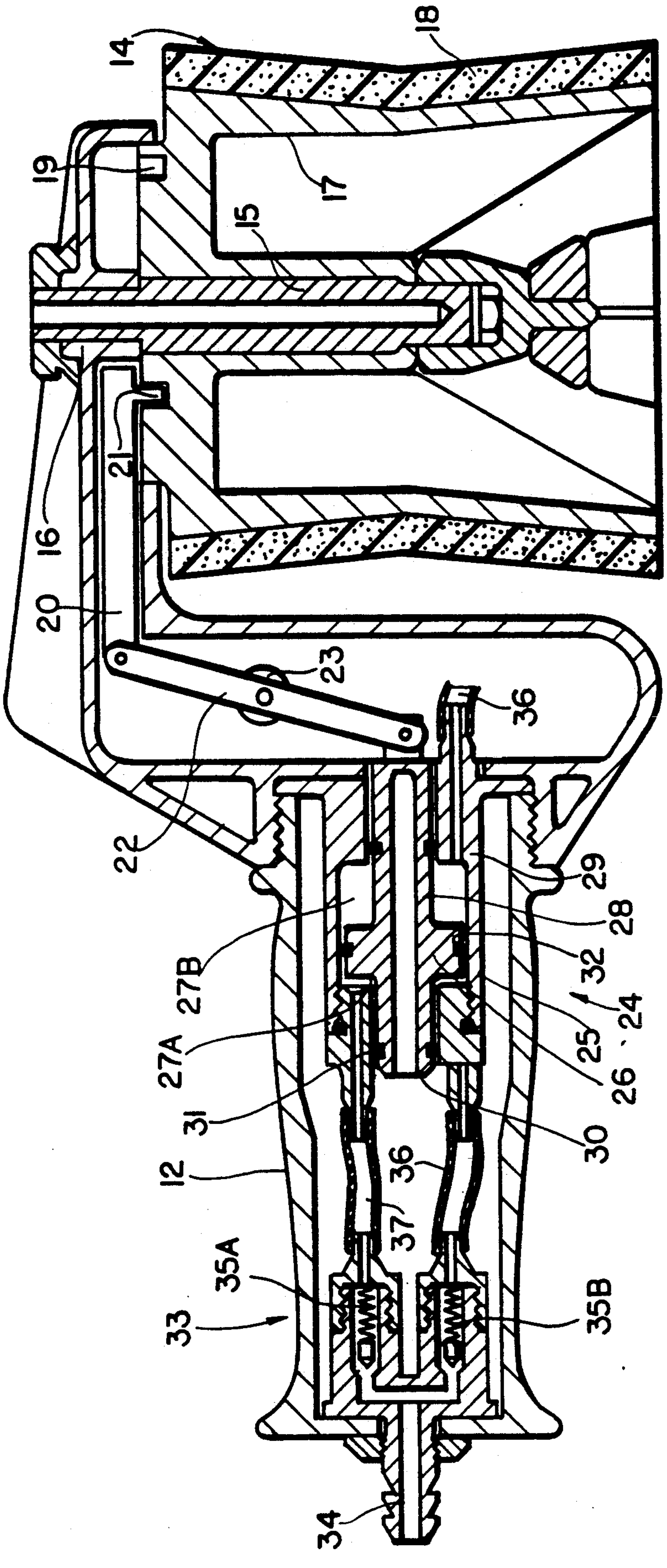
FIG. 4 is a schematic sectioned view of the applicator of FIG. 1.
Figure 6:
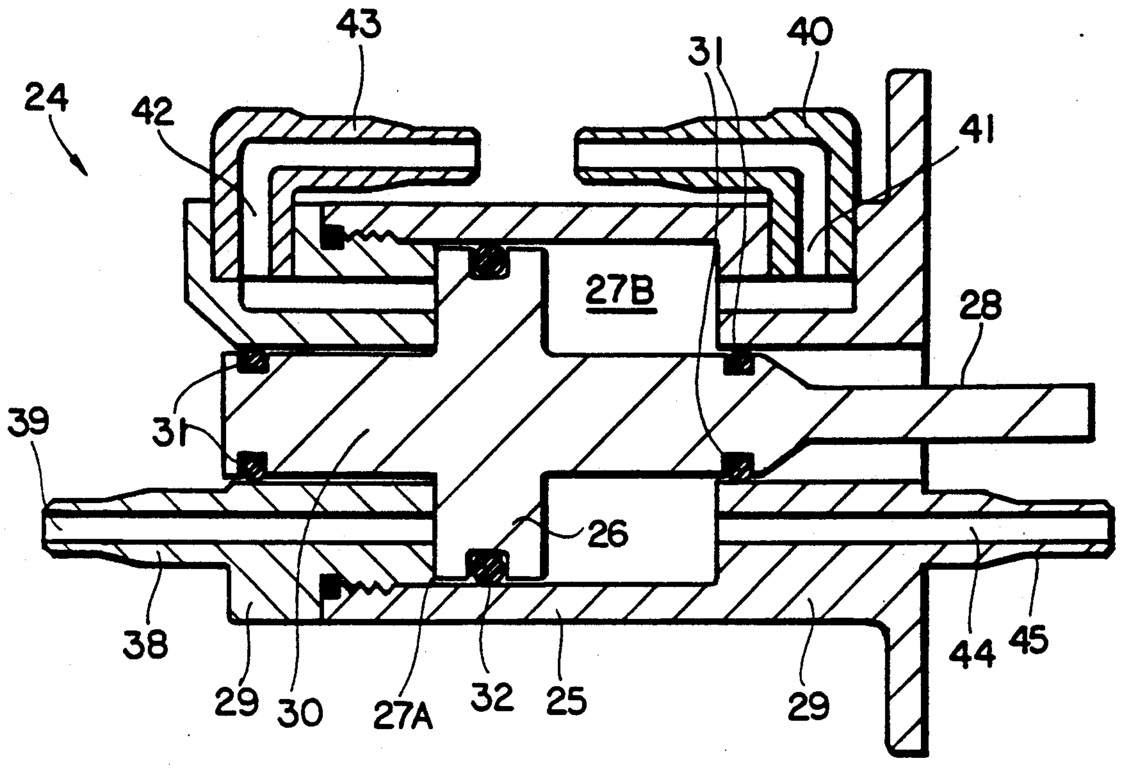
FIG. 6 is a schematic sectioned view of a pump employed in the applicator of FIG. 1.
Figure 7:
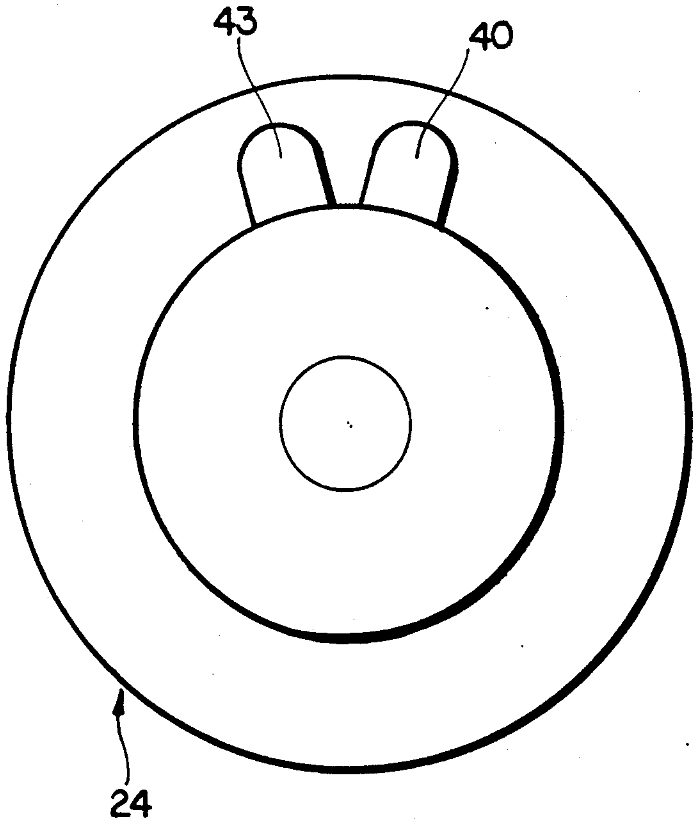
FIG. 7 is a schematic end elevation of the pump of FIG. 6.
Figure 8:
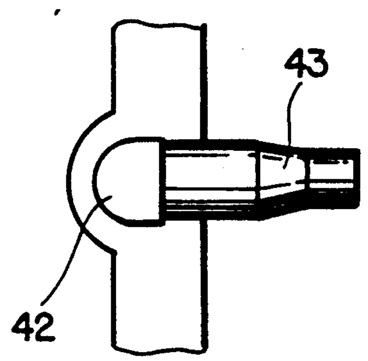
FIG. 8 Is a schematic top Plan view of a portion of the pump of FIG. 6.
Figure 9:
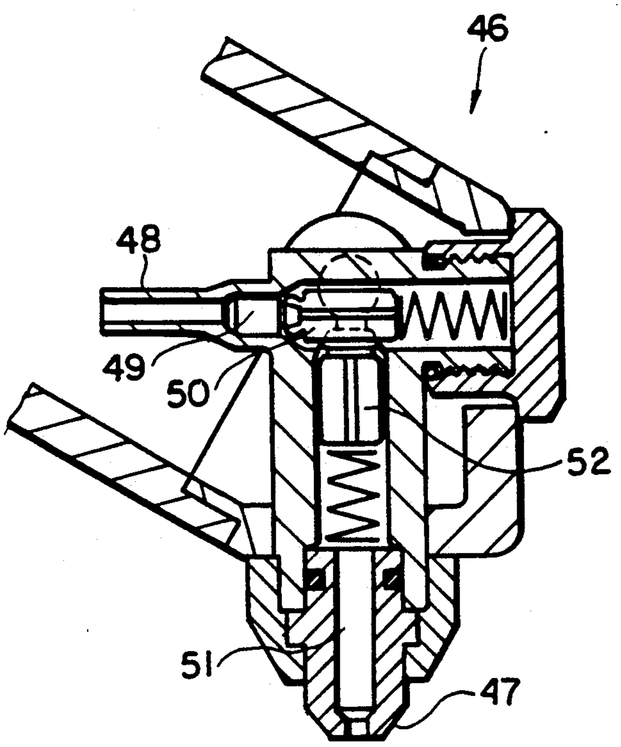
FIG. 9 is a schematic sectioned side elevation of a spray nozzle assembly employed in the applicator of FIG. 1.
Figure 10:
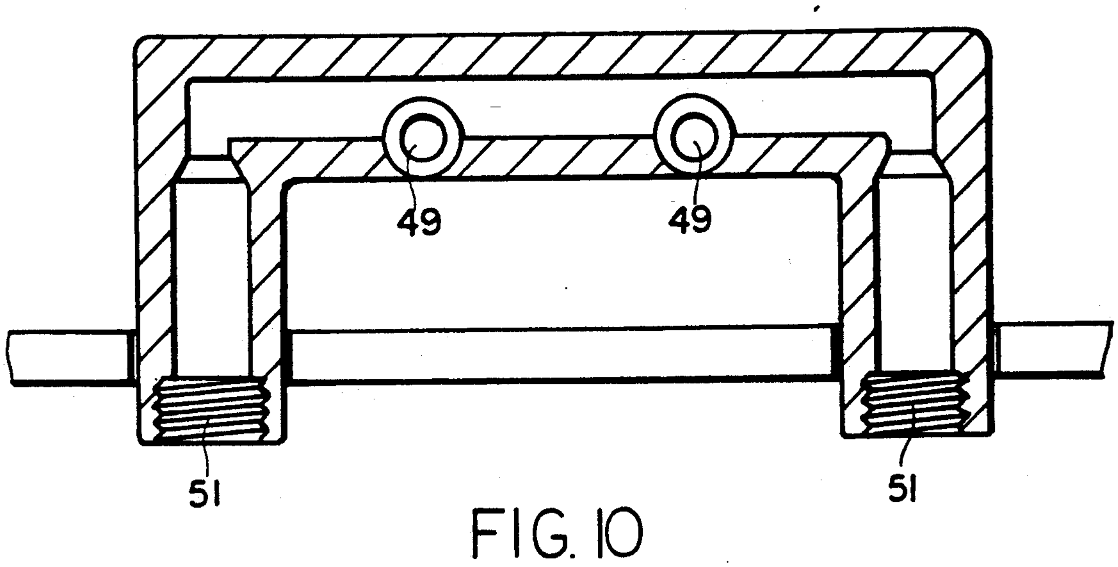
FIG. 10 is a schematic sectioned planned view of the liquid delivery system employed with the nozzles of FIG. 9.

In FIGS. 1 to 10 of the accompanying drawings there is schematically depicted an applicator 10 to deliver medication to an animal, such as a sheep. The applicator 10 has a body 11 which is hollow and provides a handle 12 to be gripped by the user. The body 11 is also provided with a forwardly extending arm 13 which rotatably supports a roller 14. The roller 14 is supported via a shaft 15 which is secured to the arm 13 and passes through a passage 16 provided by the arm 13. The roller 14 includes a hollow roller body 17 having an outer peripheral surface provided with a sleeve or coating 18. The sleeve or coating 18 would be of a material which would frictionally engage the fleece or skin of the animal. This would ensure rotation of the roller 14 when it is moved along the fleece or skin of the animal. An and face of the roller 14 is provided with a cam groove 19 which is a loop which loop, varies in radial distance from the rotational axis of the roller 14.

Slidably mounted within the arm 13 is a cam follower 20 having a projection 21 engaged within the groove 19 so that rotation of the roller 14 causes reciprocation of the cam follower 20. An extremity of the cam follower 20 is pivotally attached to a lever 22, which lever 22 is pivotally mounted intermediate its ends by means of a pivot-pin 23. The lever 22 is caused to oscillate angularly as a result of linear reciprocation of the cam follower 20.

An extremity of the lever 22 is pivotally attached to a pump assembly 24 mounted within the handle 12. The pump assembly 24 includes an interacting cylinder 25 and a piston 26, which have a longitudinal axis normal to the axis of the roller 14. The cylinder 25 and piston 26 co-operate to define two variable volume working spaces 27. Extending from the piston 26 is a piston rod 28 pivotally attached to the lever 22. Angular oscillation of the lever 22 causes reciprocation of the piston 26 to vary the volumes of the chambers 27. The piston 26 is guided In its movement by sliding engagement of the piston rod 27 in the cylinder body 29 as well as a piston rod extension portion 30 also slidably received within the cylinder body 29. Seals 31 aid in closing the chambers 27 in conjunction with the seal 32.

Operatively associated with the pump assembly 24 is an inlet valve assembly 33 also housed within the handle 12. The valve assembly 33 includes a primary inlet passage 34 which communicates via a flexible conduit to a resevoir of liquid medication. The passage 34 branches to communicate with two one-way valves 35, which one-way valves 35 restrict the flow of liquid from the passage 34 to the pump assembly 24. The one-way valve 35A communicates with the chamber 27A while the one-way valve 35B communicates with the chamber 27B. In this regard it should be appreciated that the one-way valve 35B is provided with an extended flexible conduit 36 extending to the remote end of the pump assembly 34, while the one-way valve 35A is provided with a relatively shortened flexible conduit 37 extending to an adjacent position on the pump assembly 24.

The conduit 37 extends to an Inlet projection 38 providing a passage 39 communicating with the chamber 27A. The conduit 36 extends to an inlet projection 40 providing a passage 41 communicating with the chamber 27B. Extending from the chamber 27A is an outlet passage 42, which passage 42 extends through an outlet projection 43. Extending from the passage 27B is an outlet passage 44 extending through the outlet projection 45. The conduit 36 is attached to the inlet projection 40 and the conduit 37 is attached to the inlet projection 38.

Also associated with the pump assembly 34 is a nozzle assembly 46. The nozzle assembly 46 includes one or more nozzles 47. In this particular embodiment, there are two nozzles provided. The nozzle assembly 46 includes two inlet projections 48 providing inlet passages 49. Each projection 46 is connected to an associated one of the projections 43 or 45 so that the liquid medication under pressure Is delivered to the inlet passages 49. Each passage 49 is provided with a one-way valve 50 which restricts the liquid to move from the inlet passages 49 to the nozzles 47. The inlet passages 49 extend to a gallery 50 which branches to deliver liquid under pressure to the nozzles 47 communicating with passages 51. If so required, each passage 51 could be provided with a one-way valve 52 to again restrict liquid to flow In the direction toward the nozzles 47.

Each of the one-way valves discussed above in the valve assembly 33 and nozzle assembly 46, includes a movable valve element which is biased against a seat by means of a spring. The movable valve element includes a resilient seal at its forward end to sealingly engage the valve seat. Each movable element includes longitudinally extending grooves which are exposed when the valve is moved from seating engagement with the valve seat.

The above described preferred embodiment of the present invention has the advantage of delivering medication only as a result of rotation of the roller 14. Accordingly correct quantities of the medication are metered from the applicator 10.

Figure 11:
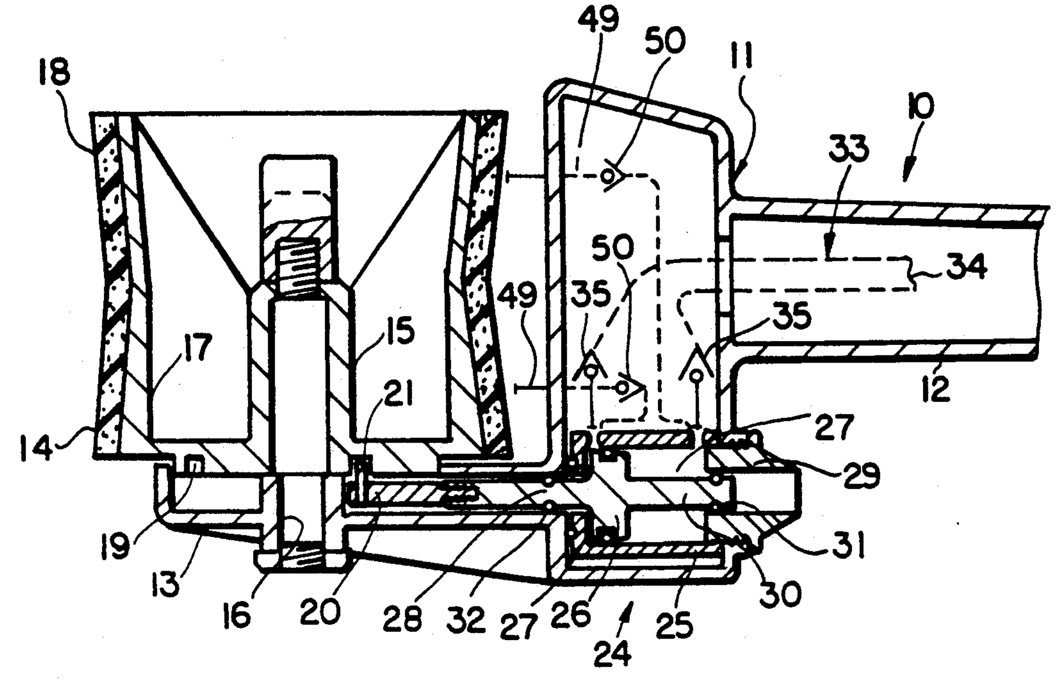
FIG. 11 is a plan view of a modification of the applicator of FIGS. 1 to 10.
Figure 12:
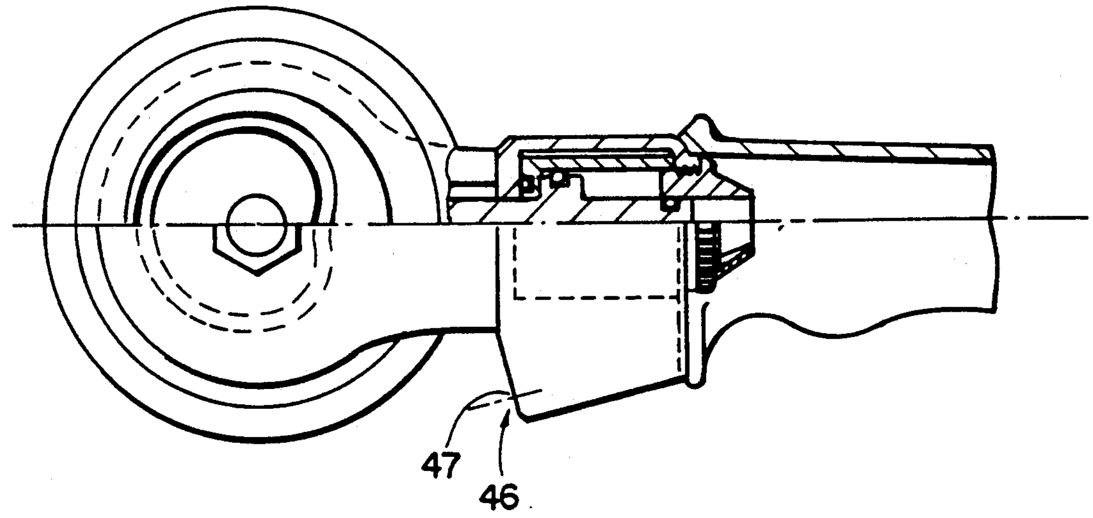
FIG. 12 is a schematic part sectioned side elevation of the applicator of FIG. 11.

In FIGS. 11 and 12 of the accompanying drawings there is schematically depicted a modification of the applicator 10. In this embodiment, the reference numerals employed correspond to those used with reference to FIGS. 1 to 10 so as to refer to the same items.

In this embodiment, the pump assembly 24 is laterally displaced from the handle so as to eliminate the need for the lever 23 and its associated pivots. The pump assembly 24 is mounted so as to be located adjacent one end cf the roller 14, and has its longitudinal axis normal to the axis of the roller 14. Also each pump element 27 would be associated with one of the nozzles 47 and associated valve 52.

What we claim is:

1. A liquid applicator configured to be totally supported by hand for applying liquid to a surface, comprising:

a body having a handle portion by which the applicator is gripped and lifted by a user;

relative movement responsive means mounted on said body and actuated by relative movement between said body and said surface upon which the liquid is to be applied, said responsive means including a rotatable element for engaging said surface and caused to rotate in response to said movement;

delivery means mounted on the body and spaced from said element, said delivery means being directed in use to deliver said liquid directly to said surface and;

pump means mounted on said body and communicating with said delivery means to deliver the liquid under pressure thereto, said pump means being driven by said element so as to deliver liquid to said delivery means upon movement of said body over said surface with said element engaged therewith.

2. The applicator of claim 1, wherein said rotatable element is rotatably mounted on said body so that upon movement of said body over said surface, said element rotates about its rotational axis.

3. The applicator of claim 2, wherein said rotatable element is a roller.

4. The applicator of claim 3, wherein said delivery means is a nozzle directed in use at said surface.

5. The applicator of claim 2, wherein said pump includes a cylinder and piston, which cylinder and piston are operatively associated with said element so that rotation of said element causes relative reciprocation between said cylinder and piston.

6. The applicator of claim 5, further including cam means operatively associated with said element to cause the relative reciprocation between said cylinder and piston.

7. The applicator of claim 6, wherein said cam means includes a cam track extending around said rotational axis, and a cam follower engaged with said track, said cam follower being restricted to perform linear motion in response to rotation of said element, said applicator further including means extending from said cam follower to cause the relative reciprocation between said cylinder and piston.

8. The applicator of claim 7, wherein said cylinder is fixed to said body, and said cam follower is fixed to said piston so as to cause reciprocation thereof within said cylinder.

9. The applicator of claim 8, wherein said cylinder has a longitudinal axis extending generally normal to said rotational axis.

10. The applicator of claim 9, wherein said element is a roller, and said cylinder and piston are located adjacent one end of said roller.

11. The applicator of claim 9, wherein said element is a roller, and said cylinder and piston are located so as to be positioned generally longitudinally centrally with respect to said roller.

12. The applicator of claim 11, wherein said handle portion has a longitudinal axis extending generally normal to the rotational axis of said element, and wherein a transverse portion extends from said handle generally parallel to said element, an arm extends from said transverse portion generally parallel to the longitudinal axis of said handle, and wherein said element is rotatably mounted on said arm.

13. The applicator of claim 12, wherein said cylinder and piston are aligned with said arm so as to be generally co-extensive with respect thereto.

14. The applicator of claim 12, wherein said cylinder and piston are located within said handle.

15. The applicator of claim 9, wherein said cylinder and piston are arranged so as to provide two operative chambers so that said piston pumps fluid to said delivery means in both stroke directions of movement of the piston.

16. The applicator of claim 9, further including valve means to restrict the flow of fluid through said pump means to said delivery means.

17. A hand held applicator to apply a liquid to an animal, said applicator comprising:

a body including a handle to be gripped by a user;

a rotatable element rotatably mounted on said body for rotation about an axis;

a pump mounted in said handle;

device means mounted on said body and coupling said element and said pump so that rotation of said element causes operation of said pump;

at least one nozzle mounted on said body and which in use is directed at said animal;

first duct means extending from said pump to said nozzle; and further duct means to deliver said liquid to said pump so that upon rotation of said element said liquid is delivered under pressure so said nozzle by operation of said pump and via said first duct means.

18. The hand held applicator of claim 17, wherein said pump includes an interacting piston and cylinder, which piston and cylinder have a longitudinal axis extending generally normal to the rotational axis of said element.

19. The applicator of claim 18, wherein said handle is elongated in the direction of the longitudinal axis of said piston and cylinder.

20. The applicator of claim 19, wherein said drive means includes a pivotally mounted lever having one end operatively associated with said piston to cause reciprocation thereof relative to said cylinder, a link extending from the other end of said lever, said link being operatively associated with said element so that a rotation of said element causes reciprocation of said link which in turn causes angular oscillation of said lever to cause reciprocation of said piston.

21. The applicator of claim 20, wherein said element has a cam groove extending angularly about the axis of said element, and said link has a cam follower mounted in said groove so that upon rotation of said element said cam follower is caused to reciprocate.

22. A liquid applicator configured to be totally supported by hand to apply a liquid to a surface of an animal, said applicator comprising:

a body, said body having a handle by which the applicator is gripped and lifted by a user to pass the body over said surface;

a rotatable element rotatably mounted on said body for rotation about an axis;

a pump mounted in said body;

drive means mounted on said body and coupling said element and said pump so that rotation of said element causes operation of said pump;

at least one nozzle mounted on said body and which in use is directed at said animal;

first duct means extending from said pump to said nozzle;

further duct means to deliver said liquid to said pump so that upon rotation of said element said liquid is delivered under pressure to said nozzle by operation of said pump and via said first duct means; and wherein said pump includes a cooperating piston and cylinder having a longitudinal axis which longitudinal axis is spaced from said handle and extends generally normal to the rotational axis of said element.

23. The applicator of claim 22, wherein said body includes a support arm for said element, which support arm couples said handle and said element, and said drive means extends through said arm.

24. The applicator of claim 23, wherein said handle is generally elongated in a direction generally normal to the rotational axis of said element, and the longitudinal axis of said piston and cylinder extends generally parallel to the axis of said handle but is laterally spaced relative thereto.

25. The applicator of claim 24, wherein said drive means includes a cam groove in said element extending generally angularly about the rotational axis of said element, and a cam follower engaged in said groove and caused to reciprocate by rotation of said element, which cam follower is fixed to said piston to cause reciprocation thereof relative to said cylinder.

* * * * *